(12) United States Patent
Pisharodi et al.

(10) Patent No.: US 10,123,937 B2
(45) Date of Patent: Nov. 13, 2018

(54) COLD/HEAT-ASSISTED DISTRIBUTED WAVE VIBRATION THERAPY

(71) Applicant: Perumala Corporation, Brownsville, TX (US)

(72) Inventors: Madhavan Pisharodi, Brownsville, TX (US); Dinesh Rabindran, Cupertino, CA (US)

(73) Assignee: Perumala Corporation, Brownsville, TX (US)

( * ) Notice: Subject to any disclaimer, the term of this patent is extended or adjusted under 35 U.S.C. 154(b) by 0 days.

(21) Appl. No.: 15/173,999

(22) Filed: Jun. 6, 2016

(65) Prior Publication Data

US 2017/0348184 A1 Dec. 7, 2017

(51) Int. Cl.
| | | |
|---|---|---|
| A61H 23/02 | (2006.01) | |
| A61H 23/00 | (2006.01) | |
| A61F 7/00 | (2006.01) | |
| A61F 7/02 | (2006.01) | |

(52) U.S. Cl.
CPC .......... *A61H 23/004* (2013.01); *A61F 7/007* (2013.01); *A61F 7/02* (2013.01); *A61H 23/0263* (2013.01); *A61F 2007/0027* (2013.01); *A61F 2007/0044* (2013.01); *A61F 2007/0071* (2013.01); *A61F 2007/0096* (2013.01); *A61H 2023/0272* (2013.01); *A61H 2201/0207* (2013.01); *A61H 2201/0214* (2013.01); *A61H 2201/10* (2013.01); *A61H 2205/081* (2013.01); *A61H 2205/106* (2013.01)

(58) Field of Classification Search
CPC .... A61H 23/00; A61H 23/02; A61H 23/0236; A61H 23/0245; A61H 23/0254; A61H 23/0263; A61H 2023/002; A61H 2023/0209; A61H 39/00; A61H 39/007; A61H 2201/12; A61H 2201/1207; A61H 2201/1215; A61H 2201/1223; A61H 2201/165; A61H 2201/5002; A61H 2201/5005; A61M 2021/0022; A61M 2021/0005; A61M 2021/0066; A61M 21/02
See application file for complete search history.

(56) References Cited

U.S. PATENT DOCUMENTS

| | | | | |
|---|---|---|---|---|
| 4,979,502 A | * | 12/1990 | Hunt | ....................... A61H 23/02 601/15 |
| 5,895,348 A | * | 4/1999 | Hosaka | .............. A61H 23/0236 600/27 |
| 6,511,446 B1 | * | 1/2003 | Wu | ........................... A61F 7/02 601/15 |
| 6,554,787 B1 | | 4/2003 | Griffin et al. | |
| 7,094,210 B2 | * | 8/2006 | Saveliev | .............. A61H 9/0078 601/1 |

(Continued)

OTHER PUBLICATIONS

Written opinion and search report dated Sep. 8, 2017 for co-pending PCT patent application No. PCT/US2017/035397.

*Primary Examiner* — Michael Tsai
(74) *Attorney, Agent, or Firm* — D'Ambrosio & Menon, PLLC; Usha Menon

(57) ABSTRACT

Methods and systems for providing pain therapy by utilizing cold/heat-assisted distributed vibration therapy. The pain therapy device includes a plurality of vibration motors that are located along a grid. The device is portable and can be adaptable to the body part requiring pain therapy.

22 Claims, 15 Drawing Sheets

(56) References Cited

U.S. PATENT DOCUMENTS

| | | | |
|---|---|---|---|
| 7,189,252 B2* | 3/2007 | Krueger | A61F 7/02 |
| | | | 607/104 |
| 8,652,189 B2 | 2/2014 | Gafni et al. | |
| 8,764,688 B1 | 7/2014 | Nauman et al. | |
| 2006/0190057 A1 | 8/2006 | Reese | |
| 2007/0232962 A1 | 10/2007 | Zumeris et al. | |
| 2010/0228304 A1* | 9/2010 | Kriksunov | A61F 7/007 |
| | | | 607/3 |
| 2011/0055720 A1* | 3/2011 | Potter | G06F 3/017 |
| | | | 715/747 |

* cited by examiner

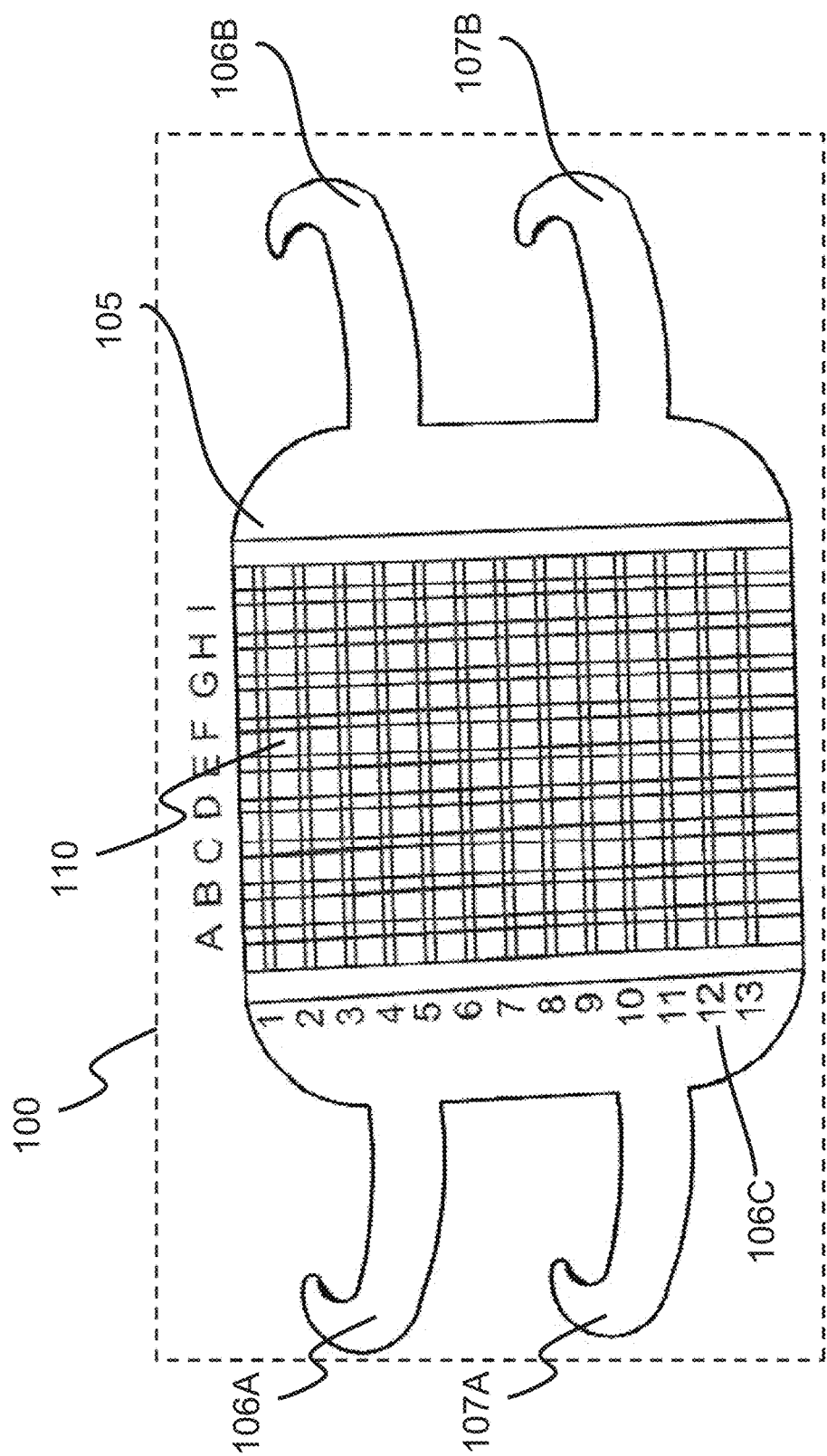

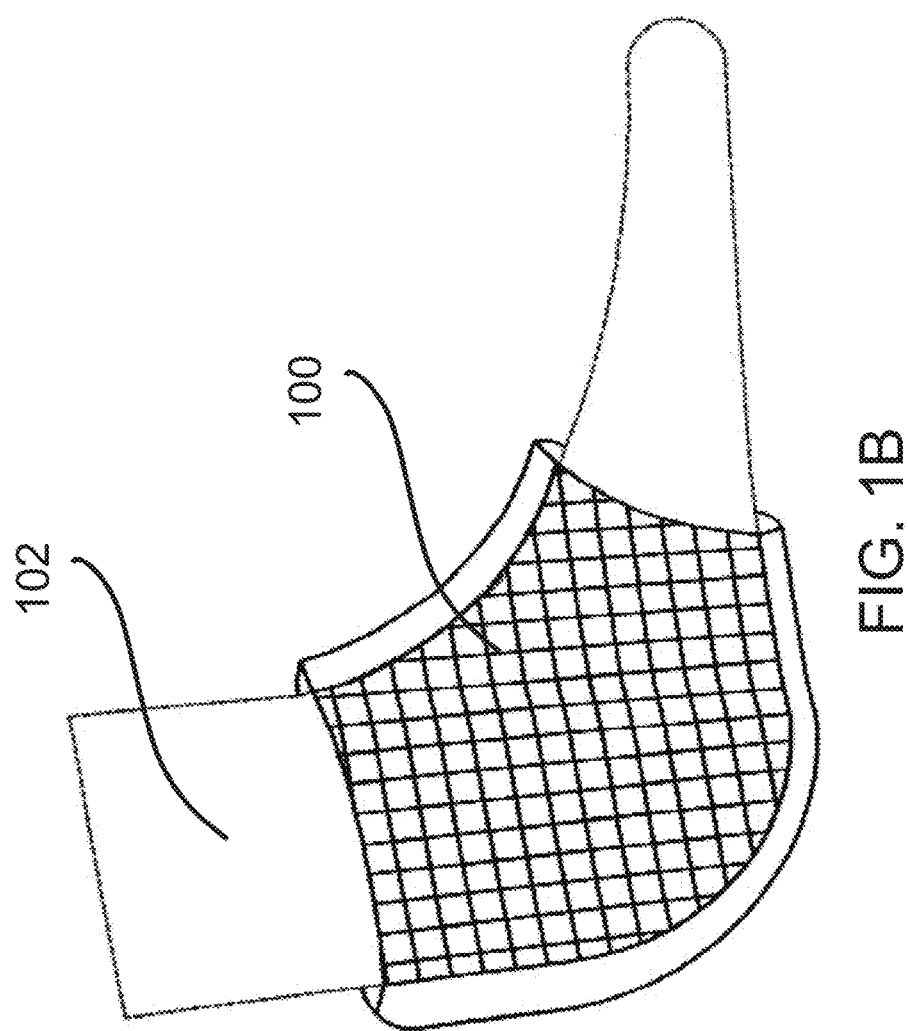

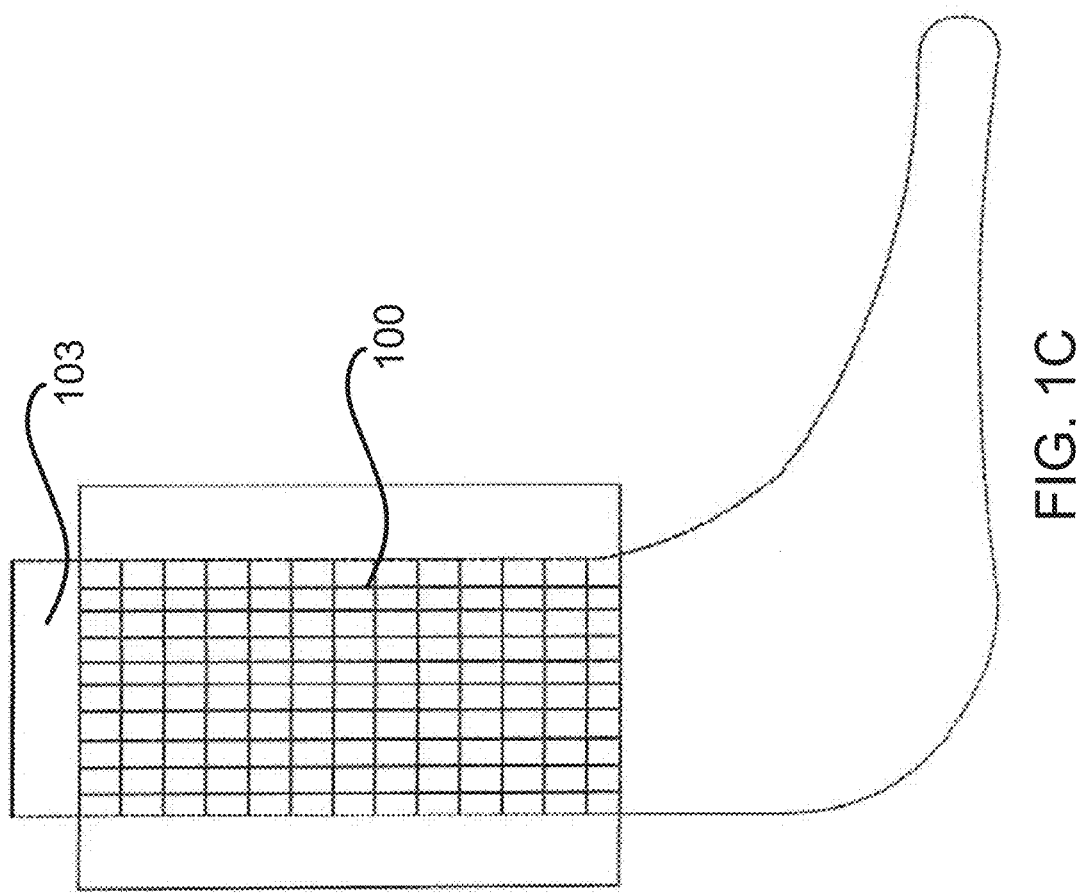

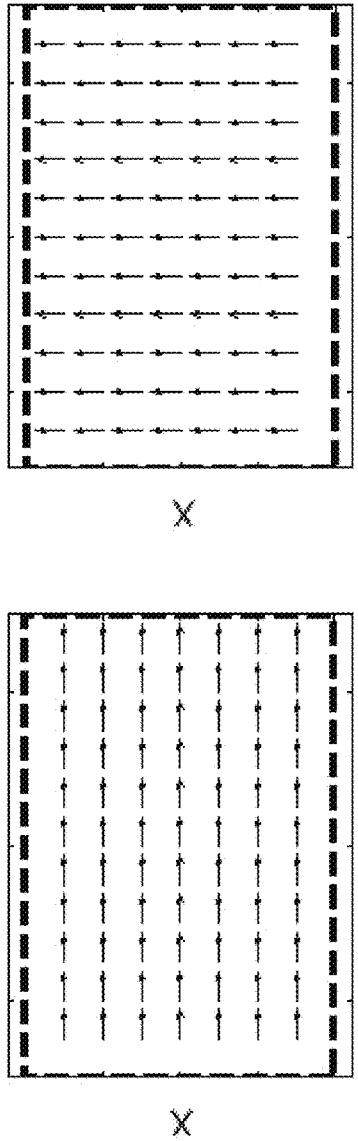
FIG. 5A
FIG. 5B
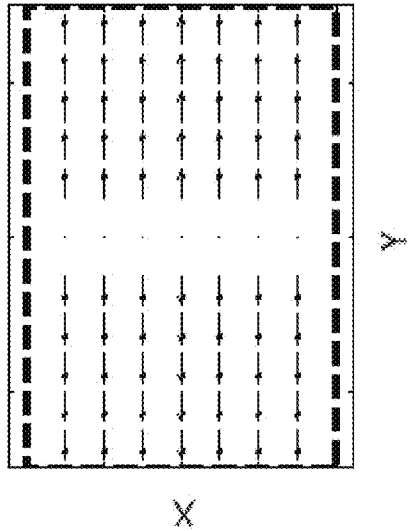
FIG. 5D
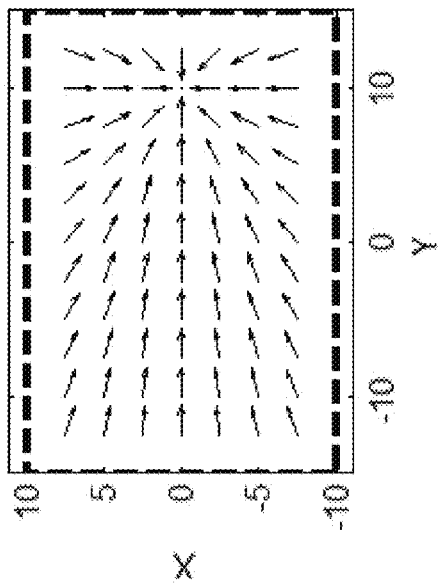
FIG. 5C

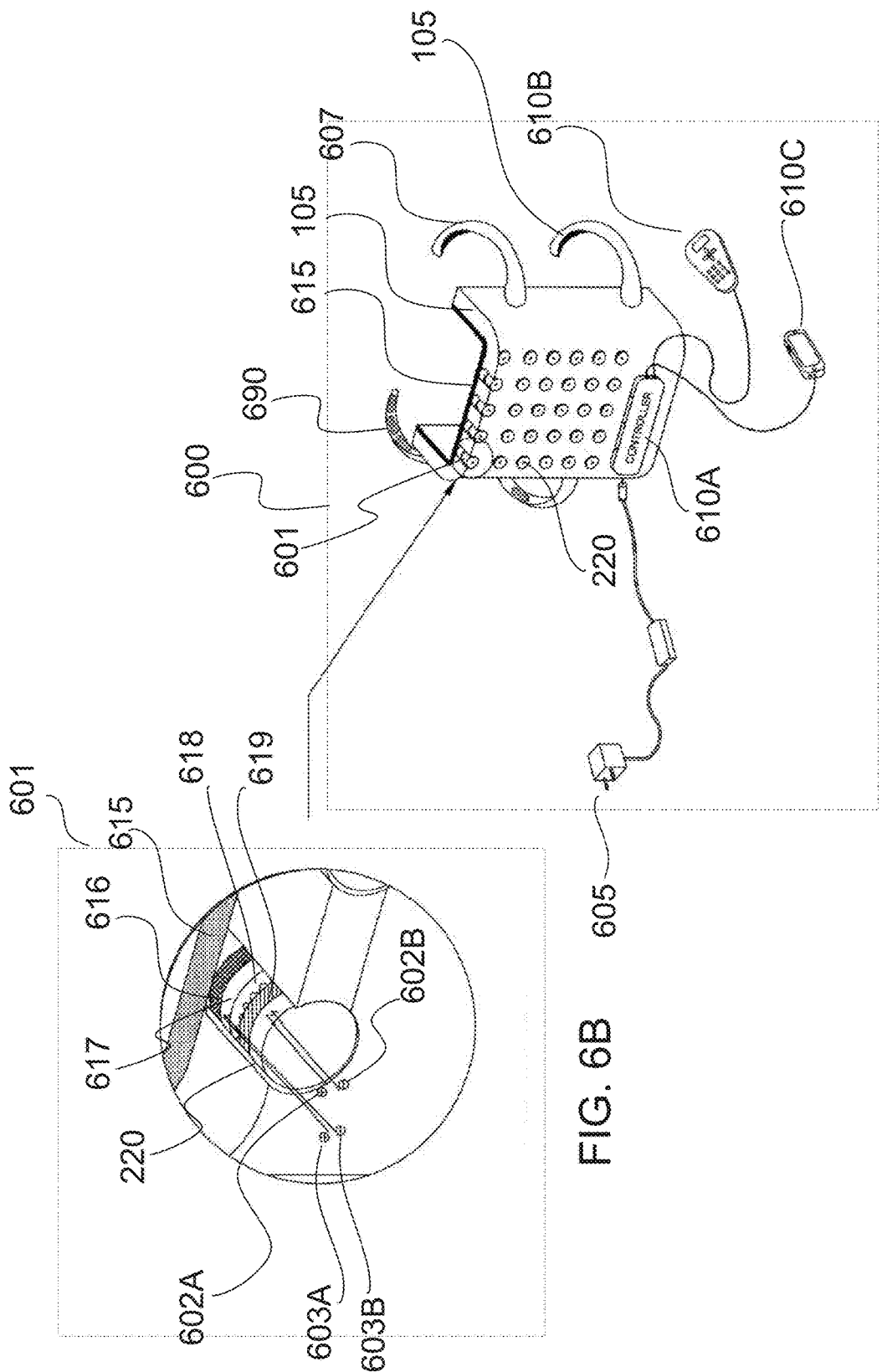

COLD/HEAT-ASSISTED DISTRIBUTED WAVE VIBRATION THERAPY

BACKGROUND

The present disclosure relates to cold- or heat-assisted distributed vibration therapy. In particular, the present disclosure relates to devices and methods for utilizing vibration therapy for beneficially manipulating pain sensation and pain perception, in addition to the mechanical stimulation.

BRIEF DESCRIPTION OF THE DRAWINGS

FIG. 1A illustrates a planar view of a wave vibration device according to an embodiment.

FIGS. 1B and 1C illustrate planar views of the wave vibration device strapped to the ankle and to the shin respectively according to an embodiment.

FIG. 5A-5H illustrates exemplary wave patterns generated by the wave vibration device according to an embodiment.

FIGS. 6A-6B illustrate a mechanical assembly of one embodiment of the wave vibration device and sectional view of the component subassembly therein.

DETAILED DESCRIPTION

Figure 2:
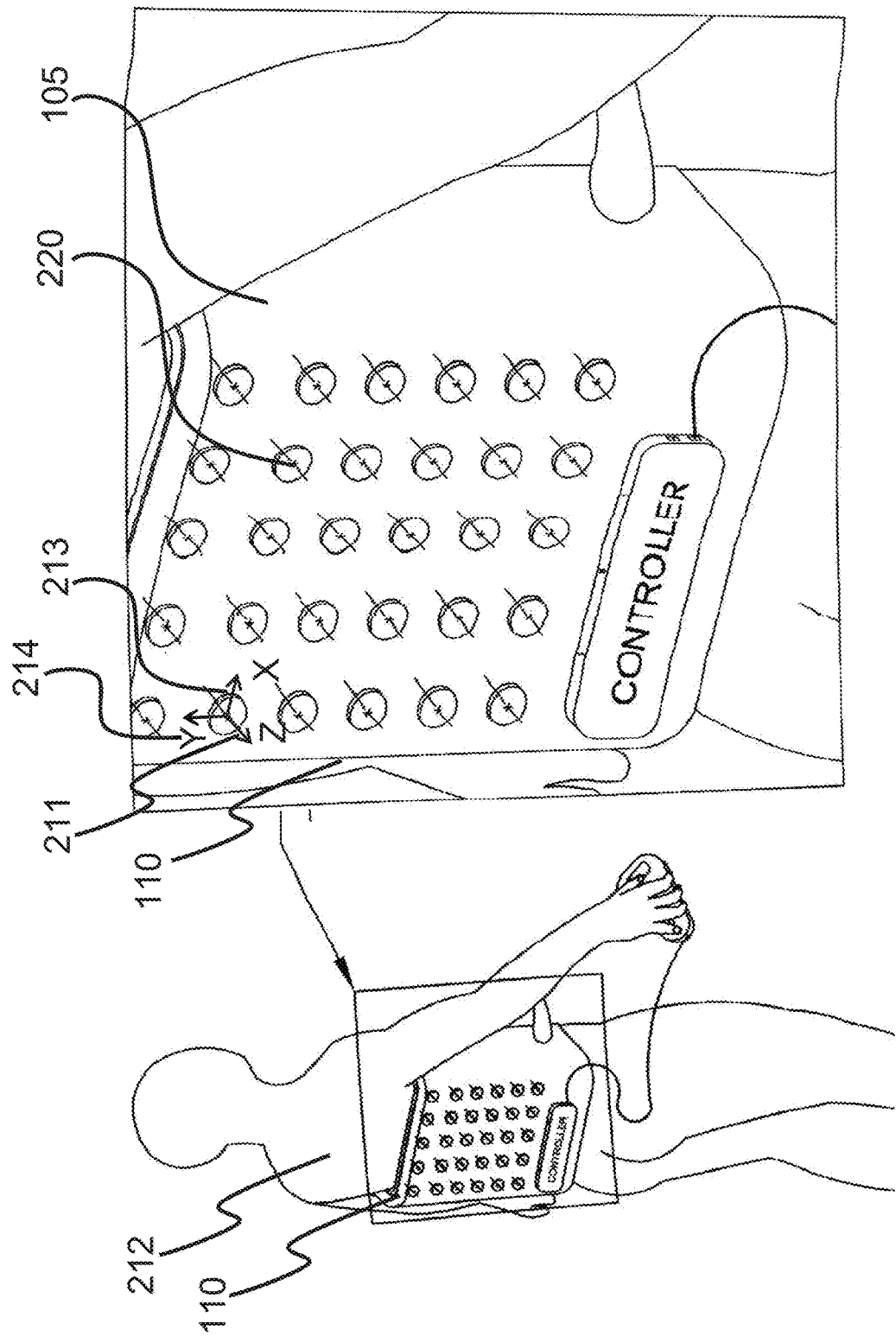
FIG. 2 illustrates a schematic view of the wave vibration device, including a vibration motor grid, worn by a user according to an embodiment.

Pain is one of the four basic cutaneous sensations like touch, pressure and temperature sense. Pain is a needed sensation to warn the individual of a harmful external influence. When pain sensation is not doing such specific function of warning and is unjustified, it is unnecessary and should be abolished. Pain, when untreated or when poorly treated, may have harmful effects on normal nociceptive pain development (that is, pain arising from the stimulation of nerve cells). It may also affect the future development of pathological pain syndromes. People who suffer with long-term or chronic pain may benefit from pain management treatments. Pain management may involve the use of pain medicine, pain therapies, or psychotherapy to help with pain relief. Pain can also be managed using mechanical or electromechanical vibratory devices. Physical vibration can provide simple pressure or can cause muscle contraction due to motor stimulation. These devices are configured to massage an affected body part to provide temporary pain relief. These massaging devices typically target a single body part, for example, the back. These devices use a few number of large vibration motors which limits their flexibility in providing various therapeutic wave patterns. These devices utilize only the local mechanical massaging quality of the vibration. Furthermore, these devices lack the ability to differentiate mechanical pressure from pain modulation.

Accordingly, there is a need for a device for masking pain that can be adapted to treat a plurality of body parts. The desired device should be capable of providing mechanical and/or sub-mechanical level of vibration sensation. The desired device should be flexible to satisfy different therapeutic regimes based on desired clinical outcomes. The desired device should be portable for convenience. The desired device should also be capable of providing cold/heat to the target body parts when desired.

Methods and systems for masking pain are disclosed herein. A pain masking/manipulation device ("device"), disclosed herein, may be used to deliver: (A) a synthetic sensation of vibration to modulate the perception of the pain at the brain or spine level; and/or (B) mechanical vibrations. The synthetic sensation of vibration and/or mechanical vibration may involve a plurality of therapeutic wave patterns.

Utilizing a synthetic sensation of vibration to modulate the perception pain involves blocking the spread of pain sensation up the spinal cord to the brain. The "gate control" theory of pain modulation states that stimulation of nerves that do not transmit pain signals (non-nociceptive fibers) can interfere with signals from pain fibers (nociceptive fibers), thereby inhibiting pain. The large diameter myelinated sensory fibers carrying the vibration sense faster can crowd and block the pain sensation carried through the much smaller diameter unmyelinated fibers conducting very slowly. The method for masking pain using the synthetic sense of vibration may further involve specifying a vibration amplitude and frequency. The vibration sensation can be enhanced by suitable heating or cooling means. The method may further involve specifying a temperature at which the sensation of vibration is optimally utilized.

Conventional mechanical devices are purely massage devices. On the contrary, the device disclosed herein can be used to mask pain by generating mechanical and/or sub-mechanical vibrations by a plurality of therapeutic wave patterns to modulate pain perception. The generation of sub-mechanical vibrations using therapeutic waves involves generation of waves of different patterns that can travel in different directions. For instance, the waves may be substantially sideways or horizontal waves, substantially vertical waves, an inward wave that can travel from the extremities toward a trigger point where the pain may be concentrated and a ripple wave that can travel outward from a single trigger point. A combination of these patterns or other relevant patterns can be provided. The pattern of the therapeutic waves may be specified or customizable by a user. The user can also specify an amplitude and frequency of the wave pattern and a location of focal point for the specified wave pattern. The user can pre-program the device with the specified wave patterns and can also review and modify the pre-programmed wave patterns. The method for pain masking using sub-mechanical vibrations further involves means to provide a decay time between successive stimulations. The vibration sensation can be enhanced by suitable heating or cooling means. The method may further involve specifying a temperature at which the sensation of vibration is optimally utilized.

The device is a novel pain masking/pain manipulation device. The device can generate mechanical wave patterns and/or sub-mechanical or synthetic vibrations to mask the pain sensation at a target body part. Vibration can be a mechanical process with intermittent compression of a body part. These are typically lower frequency larger amplitude vibrations known to be kinesthetic inputs. Vibration can also be a form of sensory sensation at the surface of the body. These are normally higher frequency lower amplitude vibrations. Sensory vibration is a "synthetic sensation" and is produced by a combination of cutaneous light touch and deep pressure sensations. Advantageously, the device can be used to provide both kinesthetic and sensory forms of vibration therapy.

The simplest vibration can be uniquely defined by its frequency, which is the number of periodic oscillations occurring in one second (i.e. units of Hz), and amplitude, which is defined as one half of the total motion undergone by the body or medium during such periodic motion. More complex vibrations could result from superposing many simpler vibrations, comprising oscillations of various amplitudes and frequencies. As used herein, a wave is an undulatory or to-and-fro movement or one of a series of such movements passing along a surface or within a medium. The target body part can be a generalization like the back or the neck, or can be specific, if the individual has a specific point of pain and tenderness where it is referred to as a trigger point.

The device can utilize mechanical vibration for pain therapy and/or massaging and can provide a vibration sensation to mask pain perception. The device can combine large area mechanical waves with localized (and potentially much higher frequency) sensory or sub-mechanical vibrations. An advantage of the wave patterns generated by the device is that they provide a wider area of coverage on the target part. Another advantage provided by the device is that it provides a delay between subsequent stimulations (or "decay time") at a particular site to allow for the tissues to react each time the wave passes through, and overcome the problem of tissue tolerance. The tolerance can further be defeated by randomly altering the speed, frequency and amplitude of the vibration. This provides an advantage over conventional devices wherein the tissue gets adapted to continuous stimulation without a delay. The device can be configured to generate one or more prescribed or previously specified wave patterns to target trigger points with concentrated muscle pain, several symmetric or asymmetric tender points with localized stresses, or sweeping wave patterns to provide a soothing pain relief, just the sensation of vibration without mechanical vibration, and/or sensory manipulation of pain perception. Therefore, the device can be used in pain therapy regimes as a pain analgesic. The device may also be used as a massaging device, like the conventional devices. The device may be used to provide therapeutic body massages, muscular pain therapy, and sensory manipulation of pain with or without actual physical massage.

The device can include an array of vibration motors, mounted on a suitable medium, which are capable of giving out different intensities of vibration at different frequencies with or without cold/heat. As used herein, a motor is a mechanism that converts any number energy forms to mechanical energy. For example, an electric motor converts electrical energy to mechanical motion. In one embodiment, the device includes a plurality of electrical vibration motors. This device converts electrical energy into mechanical vibrations by means of an eccentric mass rotating about the motor shaft at a specified angular speed. Various types of vibration motors are known in the art. Any number of different kinds of vibration motors can be used in the device depending on the target body part.

Conveniently, the device can be used to relieve pain in different parts of the body such as neck, knee, back, and elbow. The device may be portable which further facilitates use on multiple parts of the body. The device may also be used as a bedspread or as a substantially complete or partial body wrap to cover the body or one or more parts of the body.

The device can be configured such that the user can control the spatio-temporal pattern of vibrations generated by the vibration motors, in addition to the intensity and frequency of the vibration. The device can also be configured to provide cold/heat-assisted vibration therapy.

The following is a detailed description of embodiments of the disclosure depicted in the accompanying drawings. The embodiments are in such detail as to clearly communicate the disclosure. However, the amount of detail offered is not intended to limit the anticipated variations of embodiments; on the contrary, the intention is to cover all modifications, equivalents, and alternatives falling within the spirit and scope of the present disclosure as defined by the appended claims.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Various terms are used herein. To the extent a term used in a claim is not defined below, it should be given the broadest definition persons in the pertinent art have given that term as reflected in printed publications and issued patents at the time of filing.

FIG. 1A depicts an exemplary device 100 for sensory pain masking. The device 100 can be configured to provide cold/heat-assisted vibration therapy. The device 100 can include a medium 105 that can be strapped to a target body part. The medium 105 can be configured to stretch and adjust its shape to the shape of various target body parts (not shown) and to also be capable of producing desired amount of pressure on the targeted body part. The medium 105 may be manufactured from a fabric, such as a soft fabric material, leather or any other suitable material. The medium 105 may include a central mounting region 106C—the region where the active components of the device are assembled. The medium 105 and mounting region 106C may be made of a soft and flexible material such as fabric to facilitate the device's portability. To this end, the device 100 may be rolled or folded into a compact unit for easy carrying, transport, and/or storage.

The device 100 includes an actuatable grid 110. In some embodiments, the grid 110 may be a virtual grid. The grid 110 may be located along a first surface of the medium 105. The grid 110 may include a plurality of columns and rows. As shown, the grid 100 includes nine columns, labeled A-I, and thirteen rows, numbered 1-13. Vibration motors (not shown) may be arranged along the grid 110. The grid 110 allows for uniform transfer of heat or cold to the target body part during therapy (when such assistance is utilized) and also establishes a coordinate system in which the wave patterns and vibration motions from the vibration motors can be programmed using a minimal parameter set. The grid 110 can be any shape, regular or irregular. For example, the grid can be rectangular, circular or even asymmetric. The grid 110 can also be suitably sized. Although there might be advantages to maintaining a regular spacing in the grid 110, as mentioned above, non-regular grid spacing is not excluded from the scope of this disclosure.

The fidelity of pain masking sensations depends on the spacing between the motors in the grid 110—the closer the spacing, better the fidelity of the sensation. Conceivably, however, there might be physical limits on how closely spaced the vibration motors can be due to motor size and heating considerations. Similarly, there is potentially an upper limit on the spacing between motors at which point the device 100 is rendered ineffective. However, it will be obvious to one skilled in the art that the size and shape of the grid 110 can vary without deviating from the teachings of the present disclosure.

The medium 105 may include an optional fastening mechanism. For example, the fastening mechanism may include one or more pairs of straps 106A and 106B and/or 107A and 107B, respectively. The straps, say 107A and 107B may include the fabric hook and loop (not shown), are complemental parts that can adhere to each other when pressed together. The straps 107A and 107B may include a fabric hook and loop fastener made of synthetic material.

FIGS. 1B and 1C depict other embodiments of device 100. As shown in FIGS. 1B and 1C, the device 100 can be configured for various target body parts. As shown, in FIG. 1B, the device 100 can be configured as an ankle brace to treat the ankle 102 or as, shown in FIG. 1C, the device 100 can be configured as a brace to treat the shin 103. Although not shown, the device 100 can be configured for several other form factors. For example, the device 100 can also be shaped like a glove, stocking, neck collar, back brace, or similar shapes (not shown). In another embodiment (not shown), the device 100 can also be a simple flat sheet that can be layered on a bed, sofa, etc. such as, a bedspread or a body wrap to cover the entire body.

Preferably, the device 100 is portable and can function independently in a relatively small form factor to cater to the therapeutic needs of smaller body parts such as, the neck, shin, back, knee, calf or heel. However, it is also envisioned that a plurality of devices 100 can be assembled in a relatively larger form (not shown) to function as a single integral unit that can target a relatively larger body part, such as, the back or shoulder.

Figure 10:
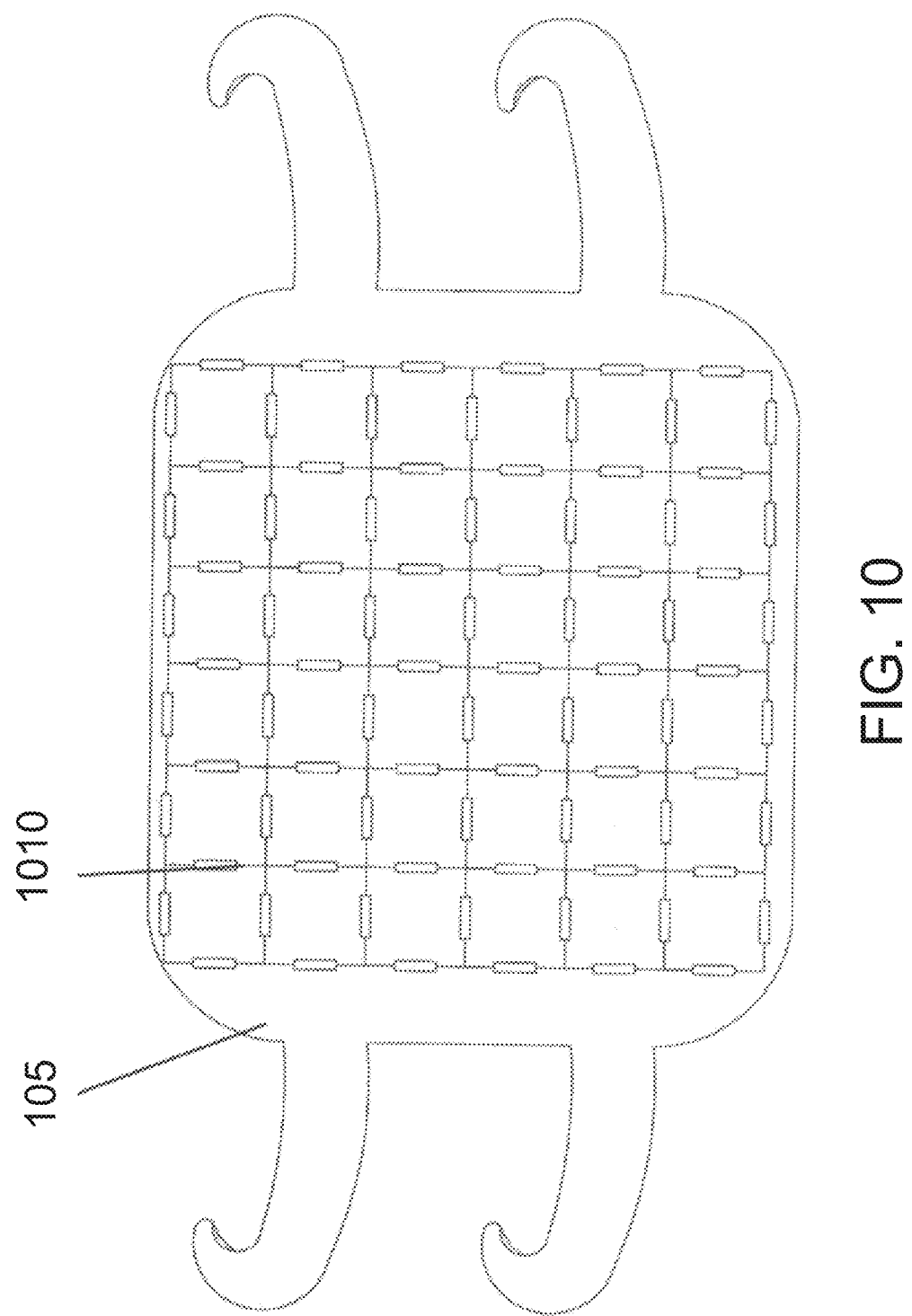
FIG. 10 illustrates a planar view of a wave vibration device according to another embodiment.

Referring now to FIG. 2, the grid 110 may be populated with an array of vibration motors 220. In one embodiment of the invention, direct current (D.C.) controlled vibration motors 220 are used. Vibration motors 220 that come in the shape of a coin or disc are preferred due to their geometry and form factor, however, depending on the embodiment, vibration motors having other shapes may be used. Alternately, as shown in FIG. 10, the medium 105 may include a plurality of small segments of a cable interrupted with junction gaps 1010. The vibration motors 220 may be arranged along various predetermined locations on the grid 110. The vibration motors 220 are the source of mechanical and/or sub-mechanical vibrations. The vibrations can be delivered at a specified frequency and amplitude. The vibration motors 220 may have motion (and impart force) perpendicular to the plane of attachment to the body, that is, in the Z axis 211, where the plane of the medium 105 and the skin of the user 212 is the X-Y plane 213, 214. The frequency and intensity of vibrations can be controlled by varying the voltage input to the vibration motors 220. One or more voltage controllers, such as, pulse width modulation (PWM) devices, variable resistors, potentiometers, or other such devices can be used to achieve controlled or programmed variable voltages to drive the vibration motors 220. As a result of such vibrations, the vibration motors 220 are capable of providing the desired mechanical and/or sub-mechanical vibrations giving the analgesic effect in their vicinity for the user 212. In addition to this sub-mechanical vibration, the timing of the voltage signal sent to each vibration motor 220 in the grid 110 can be controlled. By controlling the timing of the voltage signal, a sensation of a wave that travels along the grid 110 can be generated. This feature provides an automatic or built-in decay time to allow for tissues to react each time the wave passes through, instead of getting adapted to a continuous stimulation.

Figure 3:
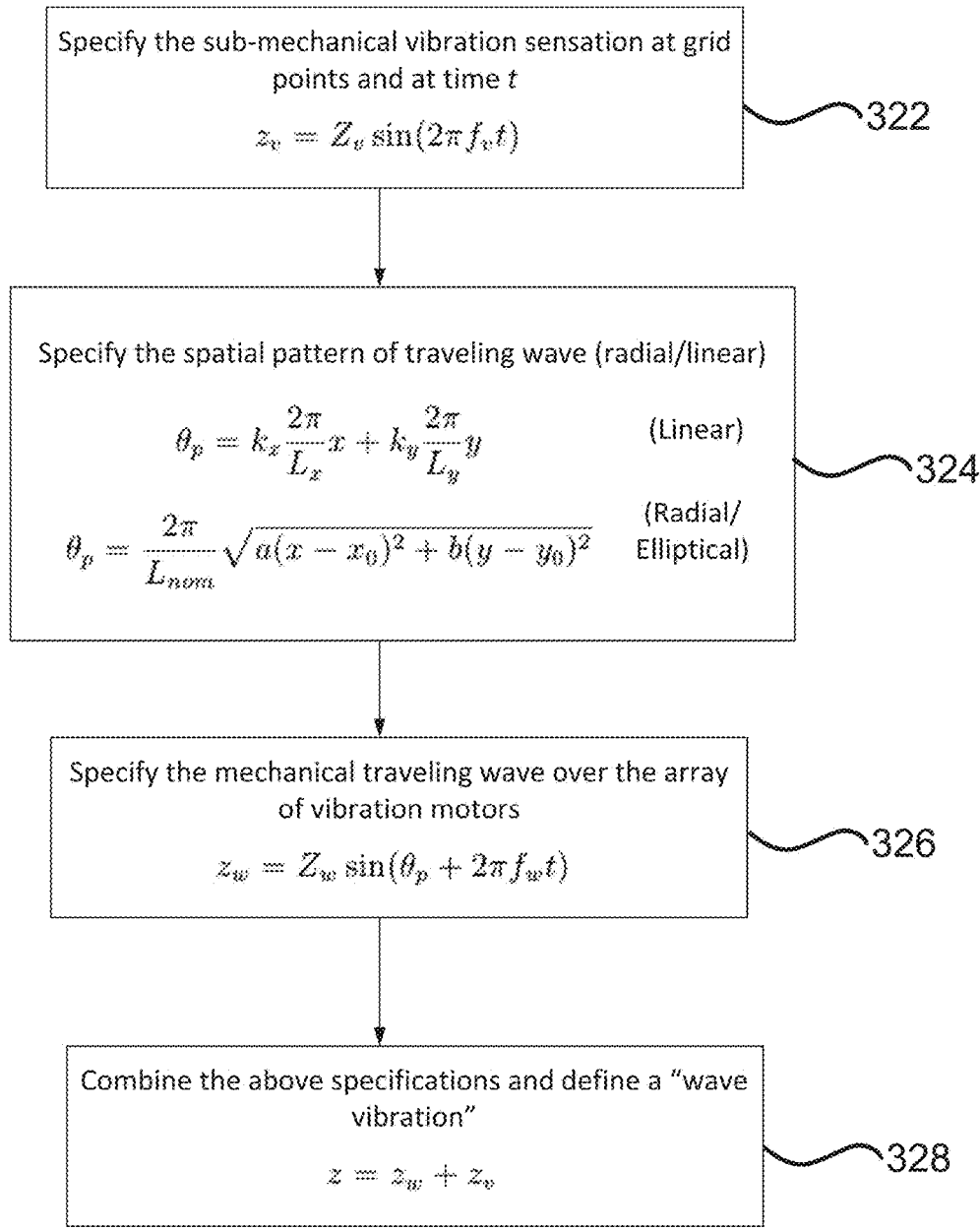
FIG. 3 illustrates a method to specify the vibrations and wave patterns used to program the wave vibration device.

FIG. 3 depicts a flowchart for controlling the motion specification of vibration motors based on time and their position in the grid. As shown in step 322, the sub-mechanical vibration of the vibration motor with respect to time can be specified as a sinusoidal signal with amplitude $Z_v$ and frequency (in Hz) of $f_v$. This is called temporal vibration in this disclosure. The temporal vibration sensation can be defined at specific grid points and at time t. Only a subset of these vibration frequencies may be clinically valuable. These clinically viable frequencies can be in the range of 50-200 Hz. However, in other embodiments, frequencies outside this band can be employed. In the next step 324, the shape of the wave pattern can be specified. For example, the wave pattern can be radial/elliptical or linear. The radial or elliptical waves can converge toward (centripetal) or diverge away (centrifugal) from a given focal or center point. The linear pattern produces a sweeping ripple along the X direction or side-to-side (213 in FIG. 2) or Y direction or up-down (214 in FIG. 2) or a linear combination of the those two orthogonal directions. In the next step 326, the specification in 324 is combined with the specification of the traveling wave's frequency $f_w$. This specification $z_w$ is called the spatio-temporal wave in this disclosure. In a final step 328, the temporal vibration $z_v$ can be combined with the spatio-temporal wave $z_w$ to define the wave vibration z. The variables and parameters shown in 322, 324, 326, and 328 can be arbitrarily chosen; however only a subset may be relevant to the desired therapy and be attainable due to power limitation of the vibration motors. The assignment of the said XYZ reference frame is arbitrary and only used herein for the purposes of specifying the elements of the device. Any frame of reference may be used to describe the vibration or wave patterns.

The above-specified motions z of the vibration motor can be felt by the user as a combination of synthetic sense of vibration accompanied by a sweeping wave or ripple train. For this purpose, the motion is specified such that the spatio-temporal wave's frequency is much lower than that of the temporal vibration, i.e. $f_w \ll f_v$. Additionally, the amplitude of the spatio-temporal wave is larger than that of the temporal vibration, i.e. $Z_w \gg Z_v$, when such control is available. Specific and basic examples of temporal vibration and spatio-temporal waves have been described, however, according to other embodiments, other generalizations may also be used. Although continuous forms of the equations are provided in FIG. 3, the vibration motors may be positioned in discrete locations along the grid and, therefore, only a sensation of a continuous wave may be created.

Figure 4A:
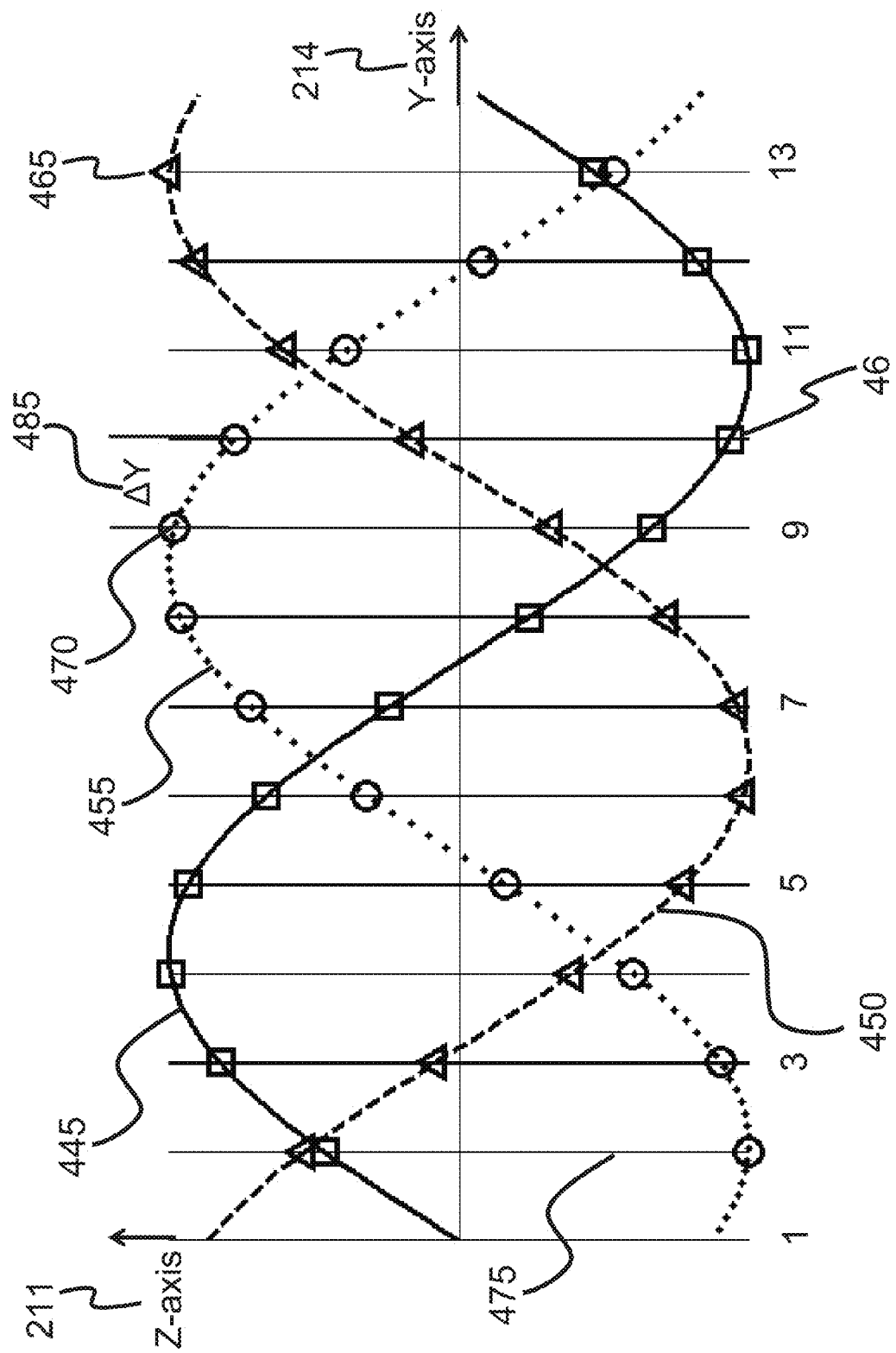
FIG. 4A illustrates an exemplary travelling wave generated by the wave vibration device purely in the Y-direction according to an embodiment.
Figure 4B:
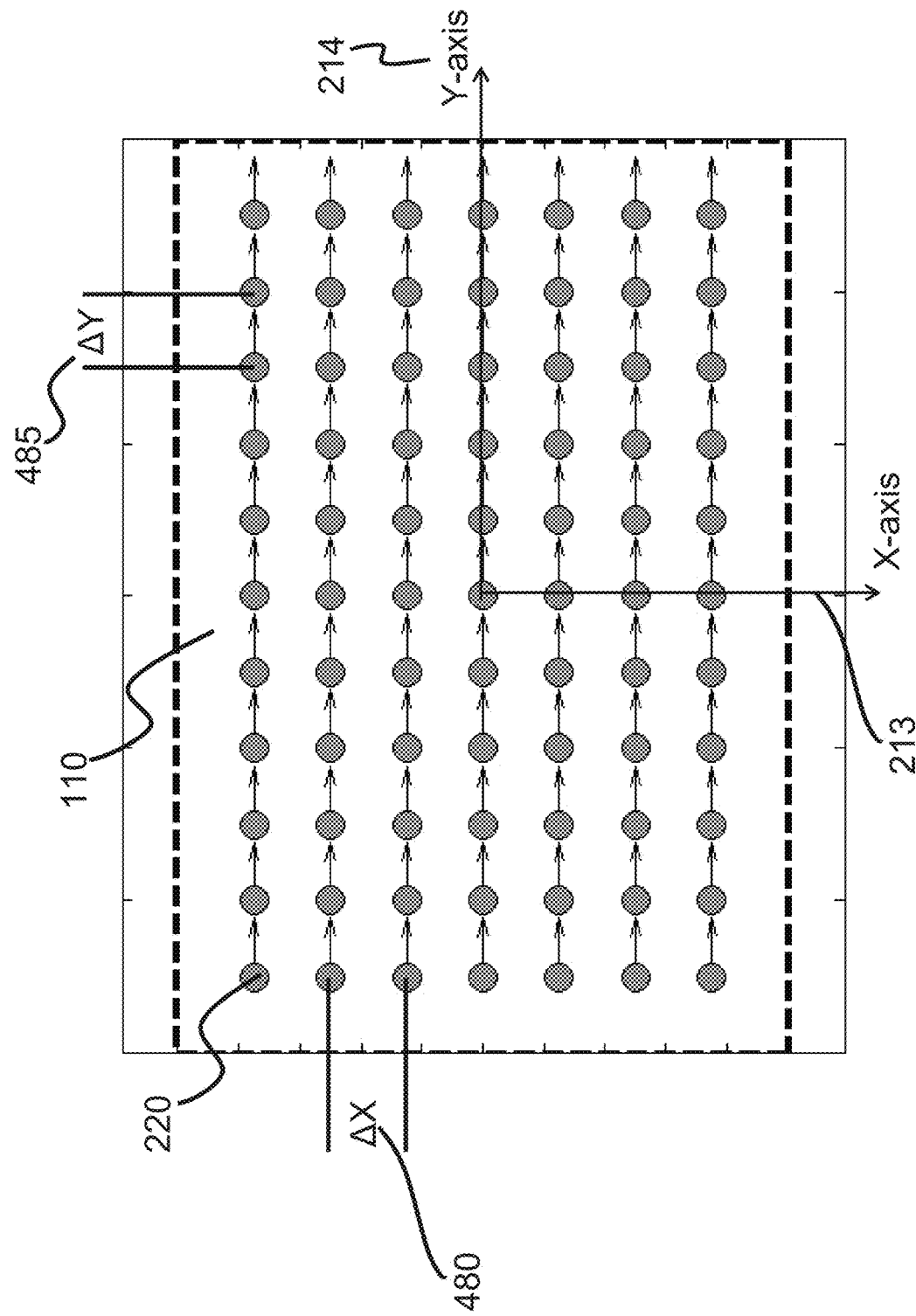
FIG. 4B illustrates the same scenario as illustrated in FIG. 4A but in the top view.

As shown in FIGS. 4A and 4B, the continuous signals defined in FIG. 3 can be discretized to render a combined sensation of a traveling wave and vibration. FIG. 4A shows snapshots of a traveling wave that may be programmed to be purely along the Y-axis 214 shown at three subsequent time intervals, 445, 450, and 455. The markers 460, 465, and 470 show the commanded or specified vibration motor amplitudes for the specific time instances of waves 445, 450, and 455, respectively. In addition to this wave, the vibration motors may also vibrate in the Z-direction 211 at a much higher frequency. FIG. 4B shows the same scenario depicted as a vector field in a top view looking down at the X-Y plane, 213-214, with the vectors showing velocity directions. The spacing between the vibration motors 220 in the grid 110, i.e. the spatial resolution $\Delta X$ 480 and $\Delta Y$ 485 shown by grid lines 475, may be dictated by the magnitude of acceleration that may be required for a particular application and tactile acuity for touch. Tactile acuity for touch is measured by two-point discrimination or the ability to discern through touch that two nearby points on the skin are distinct. In an embodiment, the voltage commanded to the vibration motors 220 dictates both the amplitude and frequency of vibration. This is because they are frequently based on an eccentric mass spinning about the motor shaft at high speeds to generate vibrations. In this motor the speed achieved by the eccentric mass increases as the motor voltage increases. This in turn determines the frequency of vibration.

Figure 5F:
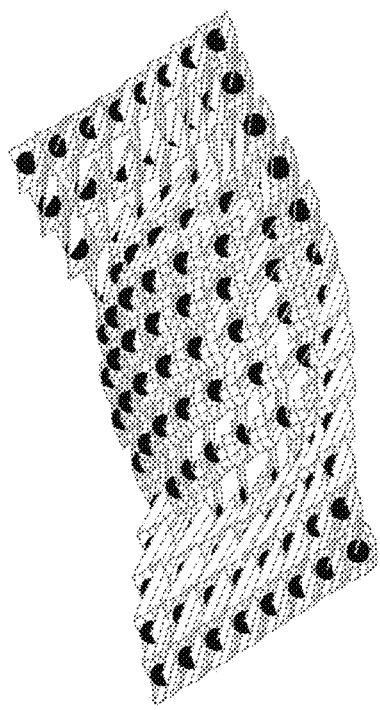
Figure 5H:
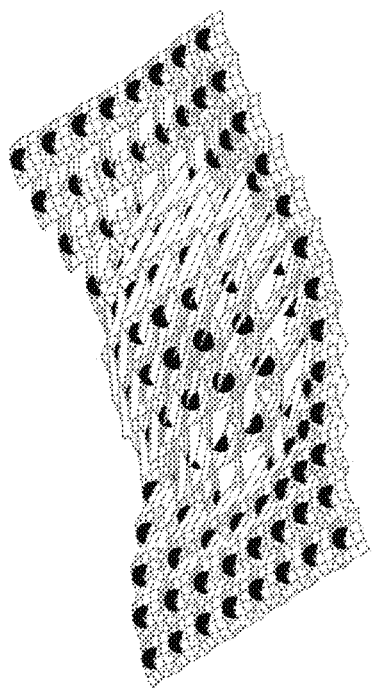
Figure 5E:
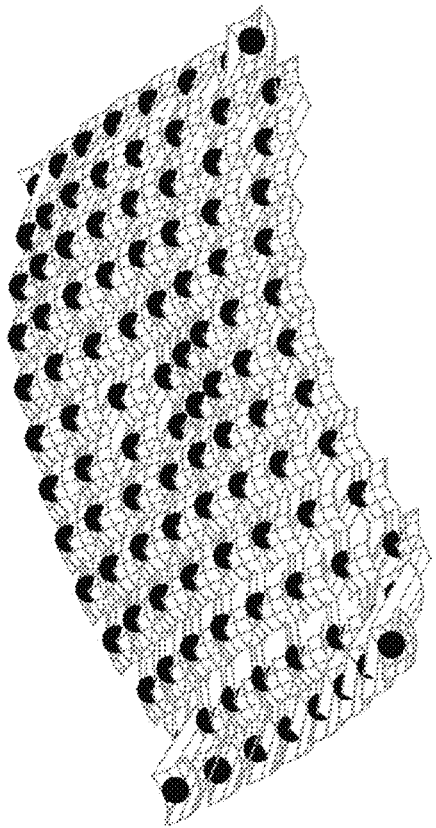
Figure 5G:
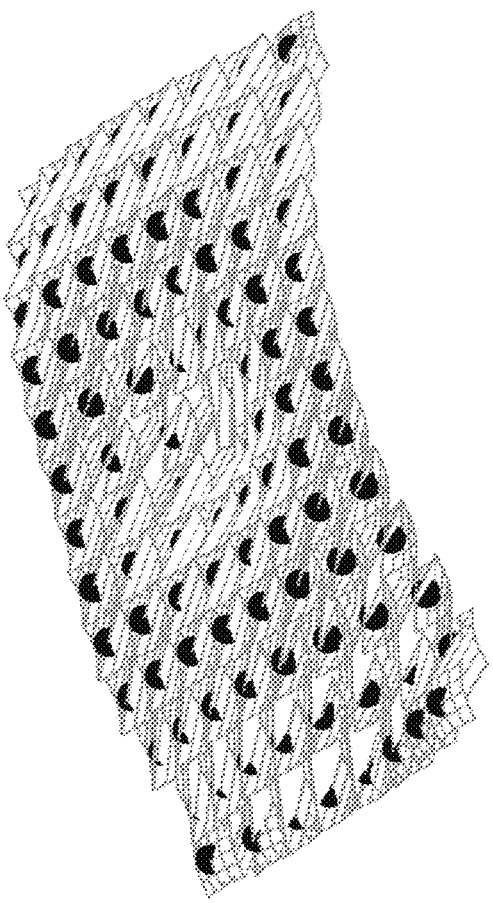

Referring to FIGS. 5A-5D, like the wave vibrations shown in FIGS. 4A and 4B, many different types of patterns can be generated using the basic methods described in FIG. 3. Exemplary patterns are shown in FIGS. 5A-5D in the form of velocity fields of the traveling wave. In FIG. 5B, the velocity pattern illustrates a pure sideways wave (wave pattern along the X-axis) in a sweeping motion from, for example, the lower back to the upper back. FIG. 5A illustrates a similar motion in a pure vertical wave form (wave pattern along the Y-axis). FIG. 5C illustrates an inward wave from the extremities toward a trigger point where pain can be concentrated. Alternately, it can be like a ripple wave that travels outward from a single point (not shown). FIG. 5D illustrates an exemplary wave pattern when the wave vibration device is strapped to, for example, the back of the neck, and where the wave travels from a central vertical line parallel to the axis of the neck to both the sides laterally. For an embodiment, FIGS. 5E-5H show isometric views of the vibration motor 120 array at four different time instances while rendering a radial traveling wave converging at the center of the grid 110 (i.e. centripetal waves). As shown and explained, the device can be programmed to provide the sensation of various general spatial wave vibration patterns.

FIG. 6A illustrates a device assembly 600 according to one embodiment of the device. The vibration motors 220 can be arranged in a grid pattern on the medium 105. The medium 105 may include a first surface comprising a soft fabric substrate. The medium 105 may further include a second surface having a thermally conductive semi-soft material 615. The device 600 can be firmly fastened or attached to a target body part using straps 607 with a suitable fastening mechanism, such as, a hook and loop mechanism 690. Such fastening provides the structural grounding to allow the vibrational force of the motors 220 to be transmitted to the user's skin via the thermally conductive semi-soft material surface 615. This surface 615 can act as a medium of attachment to the target body part and can conduct the heat/cold generated from a thermal source to the user's skin. As mentioned earlier, the sense of vibration can be used to block conduction of the pain sensation up the central nervous system. Additionally, sensory perception of vibration by the skin is enhanced by heat/cold because, firstly, the mechanical properties of the skin change with temperature and, secondly, perception channels have temperature dependence. The vibration motors 220 can be integrated with suitable heating or cooling elements in order to provide heated or cooled vibration therapy so as to exploit the said dual benefits of heat/cold and vibration.

Now referring to FIGS. 6A-6B, a thermoelectric (TE) module 617 can be positioned in series with each of the vibration motors 220 using a sub-assembly 601 for collocated vibration therapy with heating and cooling. One or more voltage controllers, such as, pulse width modulation (PWM) devices, variable resistors, potentiometers, or other such devices can be employed to achieve controlled or programmed variable voltages to set the temperature of the TE module 617. The use of a TE module 617 is not intended to be limiting. Each TE module 617 can be equipped with an open-loop mechanism to regulate to a predetermined or set point temperature. The TE module 617 can be attached to the semi-soft surface 615 using a thermally conductive adhesive layer 616, to provide a means to conduct heat from the source, that is, the TE module 617 to the destination, that is, the semi-soft surface 615. A heat sink 618 and thermal conductor 619 can provide the interface between the TE module 617 and the vibration motor 220. The heated surface of the TE module 617 can face the target body part and its cold surface can face the vibration motor 220, or the reverse arrangement can also be made. A spin-off advantage of this set up is the active cooling provided to the vibration motor 220 as the target body part is heated. The electrical connections 602A and 602B to the vibration motor 220, and the same 603A and 603B to the TE module 617 can be routed via the material 105 to a first device controller 610A. The heating and cooling elements can be independent of the vibration motors incorporated into the same medium 105.

The first device controller 610A may be a centralized controller integrated with the device 600. It could also be a standalone unit that is not integrated with the main body of the device. This first device controller 610A serves as the 'brain' of the device 600 and can include power input, circuitry, memory, electronic components (not shown) and program code for controlling or regulating the temperature of the TE modules 617 to a desired temperature setting; for the motion of the vibration motors 220; and for communicating with a second device controller 610B specified hereunder. The first device controller 610A processes inputs from the user and other sensors, and sends out commands to the vibration motors 220 and TE modules 617. The first device controller 610A can regulate a set point temperature configured by the user via a second device controller 610B. The second device controller 610B, detailed later in FIG. 7, may be connected to the device 600 (more specifically to the first device controller 610A) via a wired or wireless connection and serves as a means for the user to interact with the device 600. This specification does not preclude the use of a second device controller that is integral to the main body of the device or one that is integral to the first device controller. The distinction has been made here only to delineate the functional differences between the two controllers.

The device 600 may receive power from an on-board battery (not shown) or from an external power source via a plug connector 605. In the embodiment shown in these figures, an active heating approach is used and it may involve the integration of a temperature sensor (not shown) for safety, if not for controlling temperature. The first device controller 610A can also control the vibration motors 220. A third device controller or input device 610C could be a smart phone or other smart device. The use of such a device is described in FIG. 9. The third device controller is configurable by the user to regulate a predetermined temperature, frequency, amplitude, wave pattern, and time delay between waves. Although the second and third device controllers (610B and 610C) have been shown as separate components in this embodiment, one trained in the art can understand that these devices could potentially be combined into one input device that contains the functionality of both.

In another embodiment, the heating effect may be achieved by re-using the heat generated solely by the vibration motors 220. For this purpose, the TE module 617 and heat sink 618 may be eliminated. The thermal conductor 619 can permit a thermally conductive path from the vibration motors 220 to the target body part. In yet another approach, a hybrid approach (a combination of the active and passive approaches) can be employed to improve energy efficiency of the device 600.

Figure 6C:
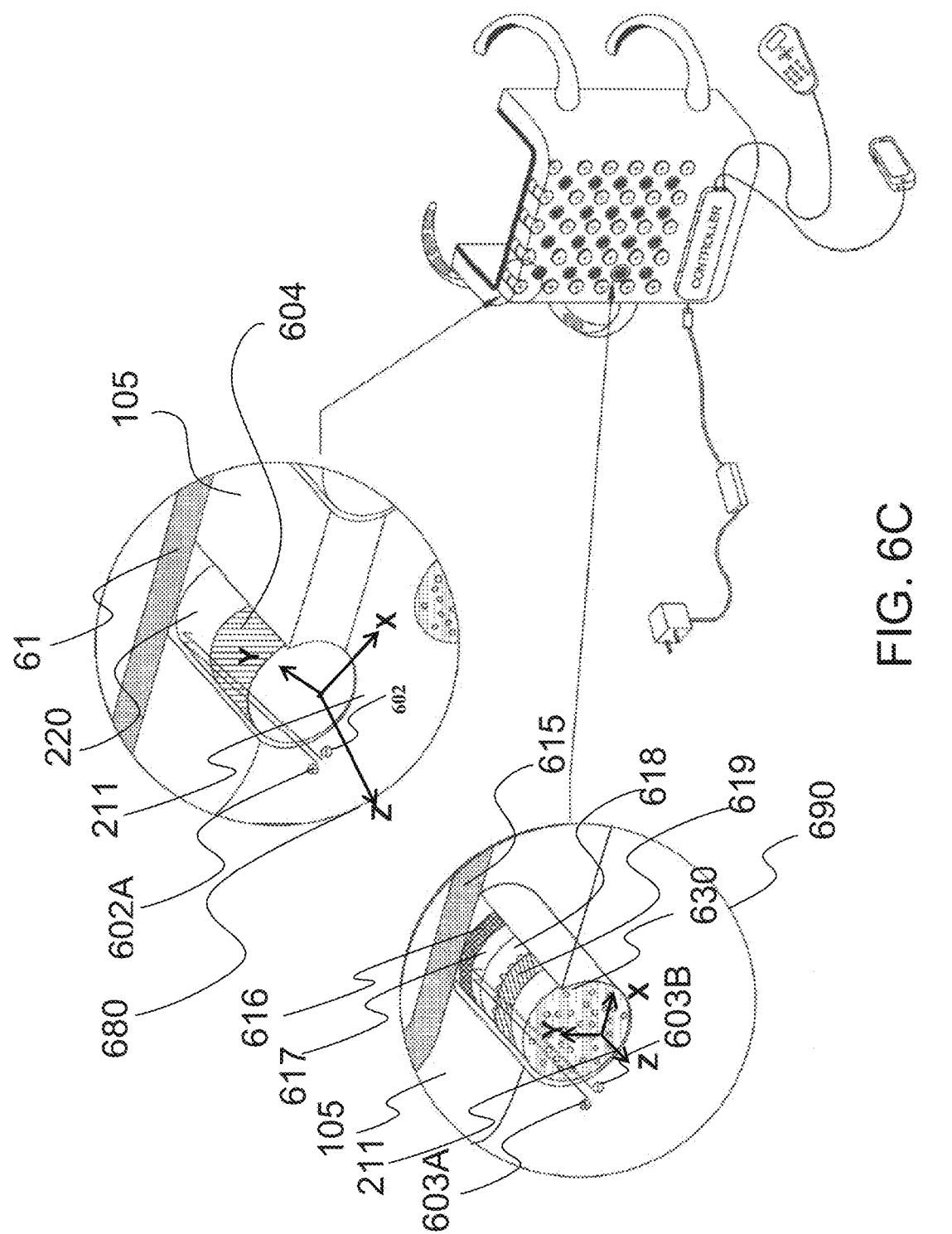
FIGS. 6C shows the mechanical assembly of another embodiment of the wave vibration device and sectional views to detail the component subassemblies therein.

In yet another embodiment to provide both heating and cooling interchangeably during operation of the device 600, the vibration motor 220 and TE module 617 may be embedded in the base material 105 in a parallel fashion for non-collocated vibration therapy with heating and cooling. This embodiment is shown in FIG. 6C, where the vibration motor 220 and the TE module 617 can both interface with the target body part in parallel via the semi-soft material 615. A spacer element 604 may be used between the outer surface (i.e. the outer surface away from the target body part) of base material 105 and the vibration motor 220, if need be. This is so that the two component subassemblies, i.e. the vibration motor sub-assembly 680 and the TE module sub-assembly 690, have the same length in the Z-direction 211. In the TE module subassembly 690, the hot surface of the TE module 617 now faces toward the external surface of the device 600 and hence provides a porous interface 630 to the exterior for transferring the heat out via heat sink 618 and a conducting interface 619. On the other hand, the cold surface of the TE module 617 faces toward the target body part via thermally conductive layers 615 and 616 to provide cooling to it. The TE module's operation principle is such that when the polarity is reversed, i.e. the positive and negative terminal connections 603A and 603B are interchanged, the hot surface becomes the cold surface or vice versa. Therefore, in this embodiment, heating may be provided as easily by reversing the polarity of the TE module 617 at connectors 603A and 603B.

According to an embodiment, a method for masking or manipulating pain involves providing a pain therapy device as described earlier. The device may be configured to provide cold/heat assisted vibration therapy. The method involves pre-programming the device, using a suitable user interface, to generate therapeutically relevant wave patterns. A plurality of input parameters may be specified according to the one or more methods described herein to define the wave patterns. The parameters may include the following: Z-dir sub-mechanical vibration amplitude $Z_v$ and frequency $f_v$ (controllable via vibration motor drive voltage); pattern of traveling wave (linear or radial). In other words, the traveling wave pattern specifies the X/Y direction spatial standing wave pattern; location of focal or trigger points if relevant for selected pattern; amplitude and speed of traveling wave determined by $f_w$, that is the X/Y direction spatial traveling wave velocity and amplitude (this spatial wave can be then discretized due to the finitely spaced location of vibration motors in the grid)—among other things, this determines the frequency of the pulse train and its intensity; and set point temperature or a finite set of temperature gradations (for example, no heat, warmth, heat, and superheat).

Figure 7:
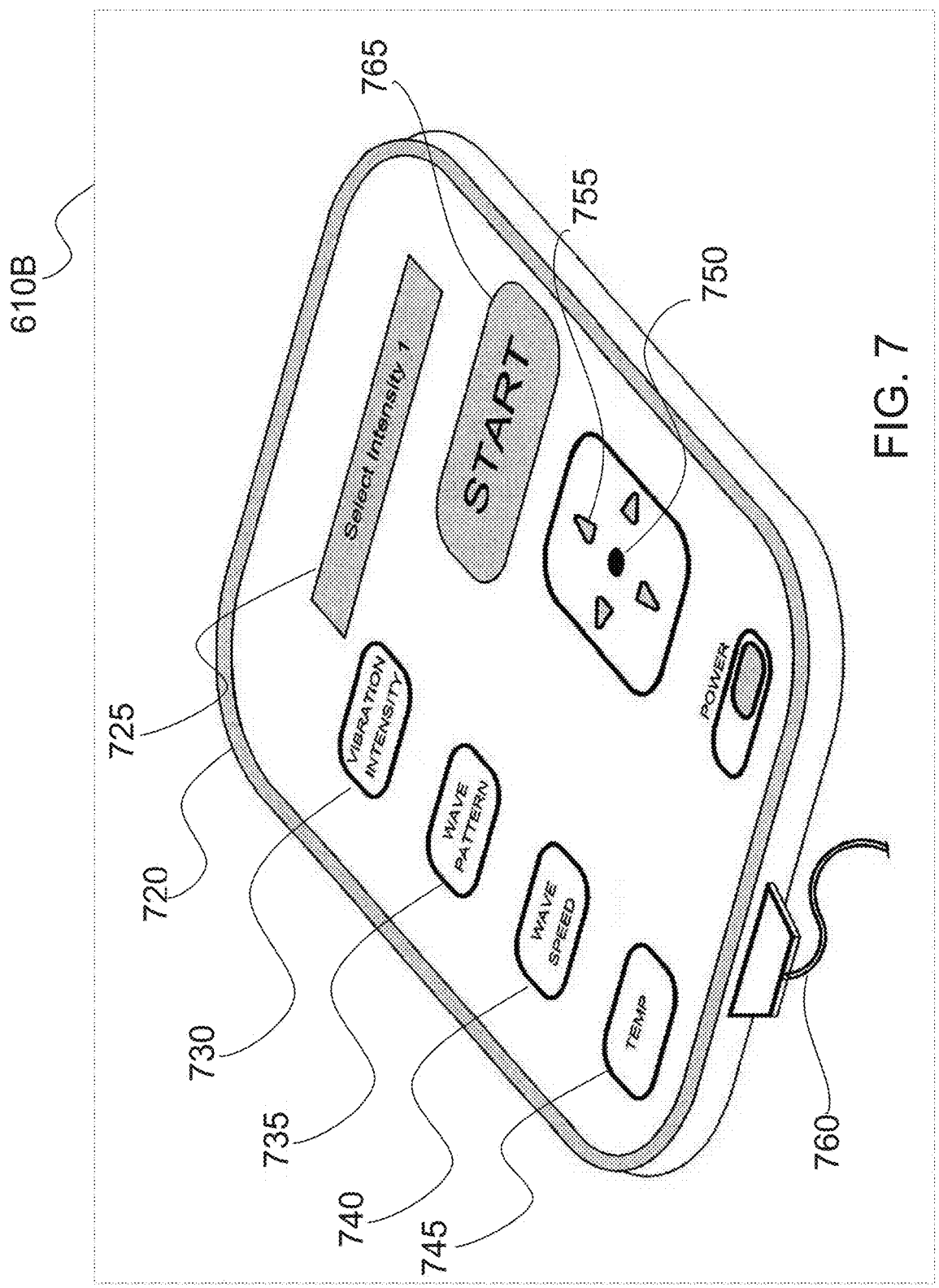
FIG. 7 illustrates a remote controller interface or regulator that functions as an input device to be connected to the wave vibration device according to an embodiment.

According to an embodiment, various appliances or gadgets can be used as a device regulator in conjunction with the disclosed embodiments. In various embodiments, the regulator can be a portable electronic gadget as illustrated in FIG. 7 (or the second device controller 610B), such as, a smart phone. Other possible gadgets can include computer tablets, portable media players, laptop computers, smart glasses, desktop computers, smart TVs, and the like. In various embodiments, such electronic gadgets can be provided with specialized or proprietary software, such as an application ("app"), program, patch, upgrade, or the like. Such a program might be made available through an "app store" or similar provider. These gadgets may be in operative communication with the device through a wired network or through Bluetooth or other wireless technology.

Referring to FIGS. 6A and 7, a second device controller 610B can include power input, circuitry, memory, electronic components (not shown) and program code for controlling and communicating with the pain manipulation/masking device 600. A user can provide a plurality of the aforementioned input parameters by using a control interface 720. The interface 720 may include a touchpad screen or a conventional panel with buttons. The interface 720 can be connected to the device using a cord 760. A vibration intensity parameter can be selected to pre-set the first device controller 610A with the desired values for $Z_v$ and $f_v$ by touching or pressing a vibration intensity mode selector button 730 once, including an option to vary the frequency and amplitude randomly over a desired range while in operation. This causes a prompting message such as "select intensity" to be displayed on a display screen 725. The screen 725 may have a LED display. In response to this prompt, the user can use the up/down buttons 755 to choose a desired intensity (displayed again on 725 as this change is made), and then press the OK button 750 to set the value. This will select the vibration intensity to be used to program the device for subsequent use. Subsequently, the "start" button (implemented as a toggle switch) can be pressed to start or resume operation with the newly set parameter. The second device controller 610B could also allow changing these parameters when the device 600 is in operation so the user can "play" a setting before selecting it to program the device. It will be obvious to a practitioner in the art that there is more than one way to achieve a given set of functionalities on a second device controller 610B, however, the second device controller 610B exposes the user to a set a parameters that can be controlled to alleviate the pain sensation in a target body part.

Figure 8:
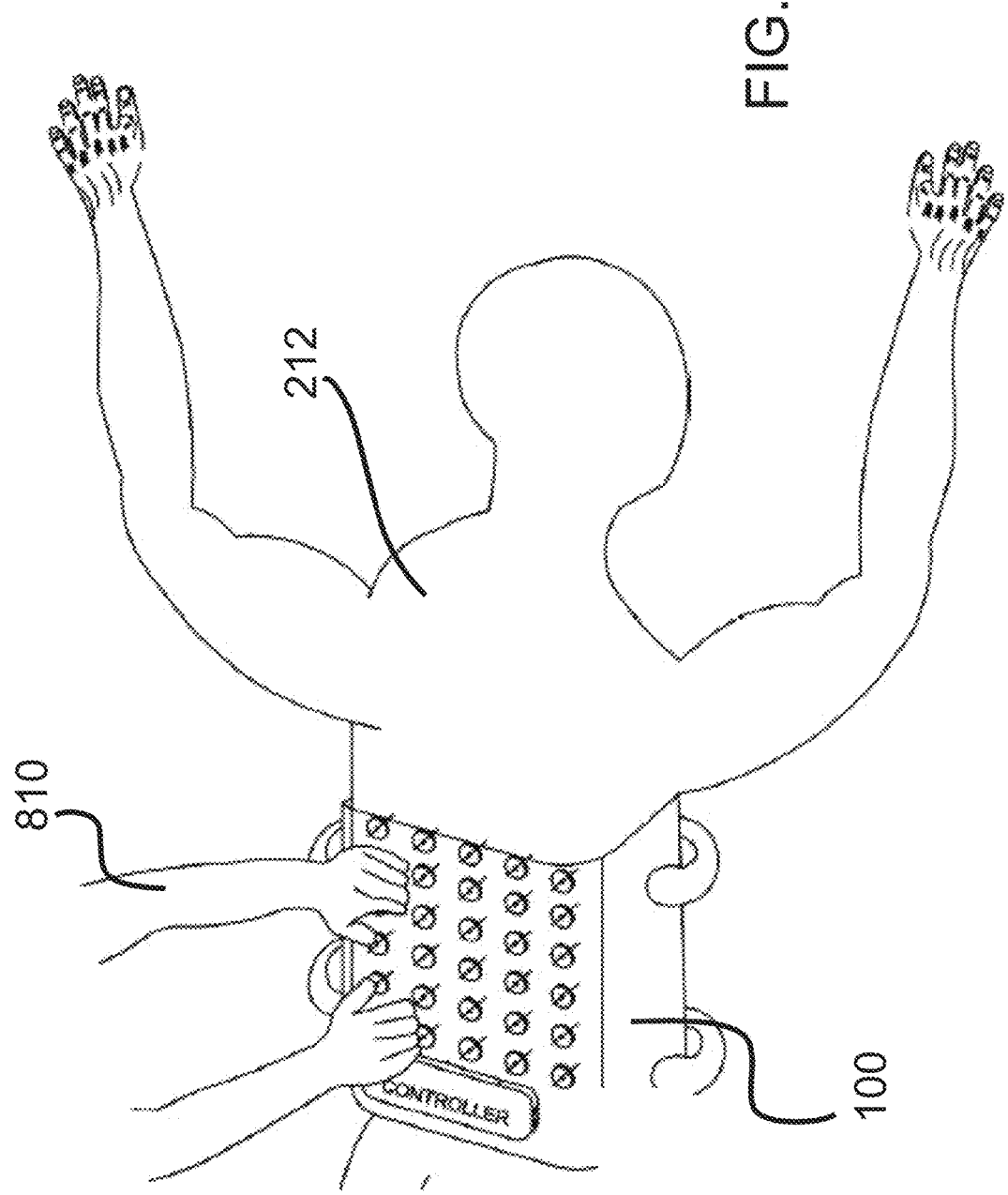
FIG. 8 illustrates a user interacting with the device physically in order to program it according to an embodiment.

As shown in FIG. 8, by facilitating physical interaction of the patient/user 212 or a therapist 810 with the device, a desired wave vibration therapy pattern (including both the motion and pressure information) can be defined for pain therapy (or a regular massage). To achieve this, the intent of the user 212 or therapist 810 can be translated into wave vibration parameters. The device 100 may be attached to the user's 212 target body part, for instance, his/her back. To 'teach' the device 100 a desired therapy pattern, the therapist or an assistant 810 could make sweeping movements with his/her palm or hand with the desired pressure. Such motion and pressure applied therefor is considered representative of the motion and pressure desired from the device 100 for subsequent therapy. Now referring to FIGS. 7 and 8, to put this device 100 in such a teach mode, a combination of buttons on the second device controller 610B can be reused.

For instance, a double press on the select button 750 may be used to indicate such a mode transition. In this teach mode, the device 100 attached to the user's back can sense and store the data associated with the wave vibration therapy pattern. This data storage function may be implemented either on the first controller 610A (as shown in FIG. 6A) or on the second controller 610B. Subsequently, the therapy pattern may be replayed by the vibration motors. Before replaying, the pattern could potentially be displayed to the user (by using LEDs assembled alongside the vibration motors, in one embodiment) for confirmation.

The motion component of the therapy pattern may be sensed according to various techniques. By exploiting the grid structure of the device's design, a projected capacitive touch technology (using a flexible substrate) may be incorporated to detect both the accurate location and pressure of the provider's interaction with the device. In another embodiment, force or pressure sensing may be integrated into the medium to sense the therapy pattern. If the spatial resolution with which the provider hand location is determined is inferior, interpolation may be used to smooth the measurements. The therapy pattern consists of time samples of grid locations that were interacted with, in addition to pressure magnitude in those locations. Consider a data point at time Ti to be represented as (Xi, Yi, Pi), where (Xi, Yi) are the touch locations in the grid and Pi is the corresponding pressure. This dataset is then used to fit the parameters of $z_w$ (shown in block 326 of FIG. 3). The magnitude of the spatial wave, $Z_w$, may be determined based on normalized values of Pi. The sub-mechanical vibration sensation amplitude and frequency may be chosen for the user by the device based on the therapy regime. This is because the vibration sensation frequencies are far higher (in excess of 20 Hz) than what a provider can apply to the device in a manual teach mode.

An alternative to choose the vibration sensation magnitude is via the vibration intensity button 730. Additionally, a temperature setting may be selected from the second device controller's 610B temperature selection button 745, if such functionality is enabled on the device. The aforementioned parameters of $Z_w$ estimated based on (Xi, Yi, Pi), together with the sub-mechanical vibration magnitude and frequency, and the selected temperature (if such functionality is enabled on the device) constitute the therapy pattern. This pattern may be stored in on-board memory (not shown) inside the second device controller 610B or the first controller 610A. The therapy pattern may be loaded to be replayed on the device using the interface 720. For instance, the wave pattern button 735 may be double pressed to enter into replay mode, and the arrow buttons 755 may be used to select the pattern to be played. These patterns can be saved in memory with an identifier string that can be displayed on 725 when in such an operational mode. The aforementioned description delineates a method for the therapist to teach and replay a therapy pattern on the device by means of touch sensing and/or force/pressure sensing technology to interact with the device.

Figure 9:
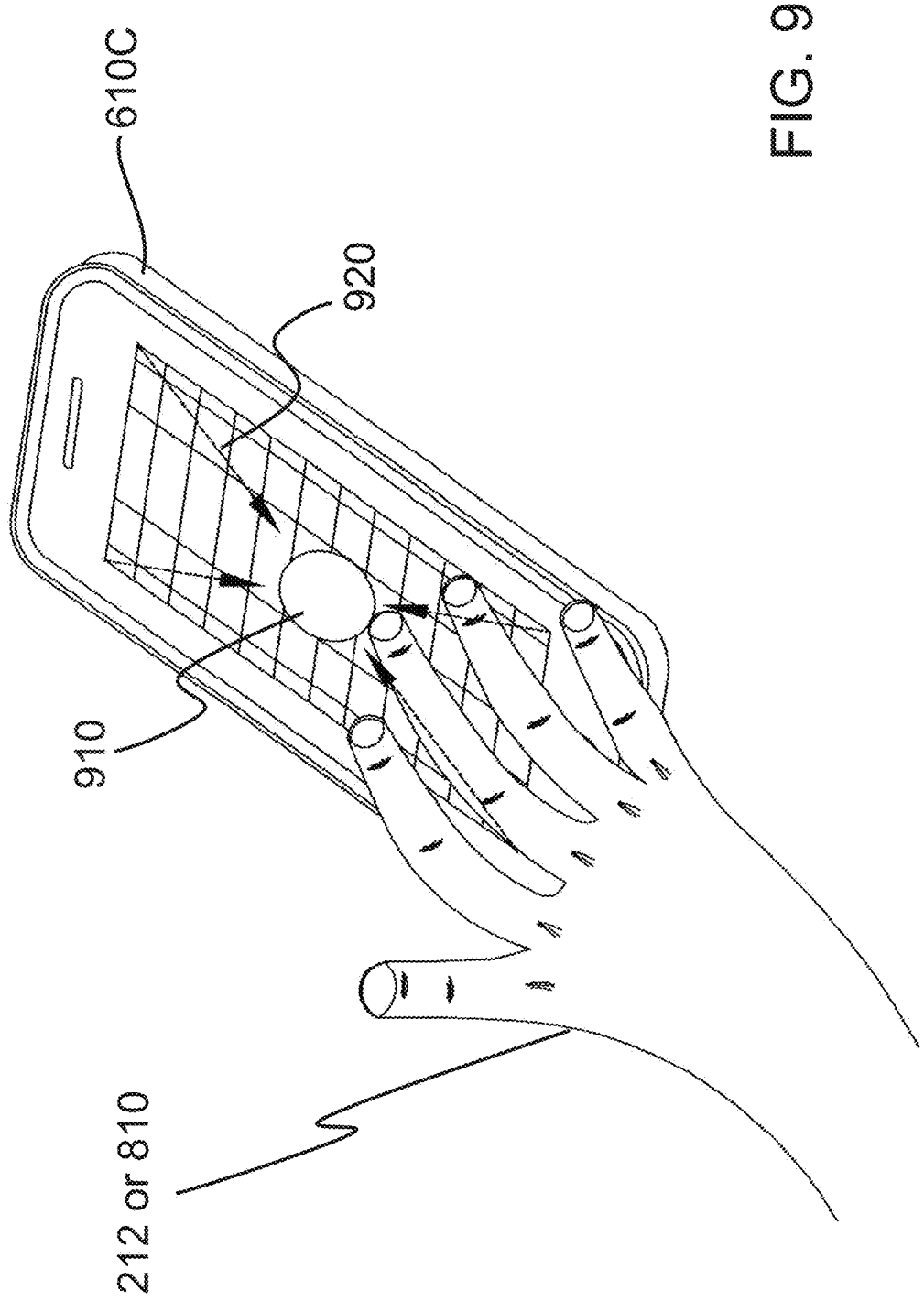
FIG. 9 illustrates a user interacting with and programming the device via a smart phone's touch pad or other similar smart device according to an embodiment.

Now referring to FIGS. 6A and 9, a method of interacting with the device 600 to specify the therapy pattern is disclosed. The method may involve a four-step process: (i) interactively generating the motion component of the intended therapy pattern by drawing on the touchpad screen of the third device controller or smart device 610C as shown in FIG. 9; (ii) shaking the smart device 610C to convey the intensity of vibration, (iii) downloading the therapy pattern using a proprietary format (herein called the pattern file) on to the first device controller 610A by interfacing to it via a USB or other appropriate connector, and (iv) replaying the therapy pattern using the first device controller 610A. In the first step, the touchpad screen sensor of the smart device 610C can be utilized to sense the motion pattern desired by the user. In this embodiment, an intended motion may be conveyed to the device by moving (example motions shown by the arrows 920) only the fingers of the user 212 (or therapist) such that it approximates an application of a therapeutic motion on a graphical representation of the target part 910. In the second step, the user may be prompted to shake the smart device 610C to indicate the magnitude of pressure applied to the target part. This smart device 610C can be programmed with an algorithm that can fit the therapy pattern parameters defining $Z_w$ (shown in block 726 of FIG. 3). In the third step, these parameters, together with pre-selected vibration intensity and frequency, can be stored on the first device controller 610A in its local memory as a pattern file. When connected to the device 600 via an appropriate interface such as a USB connection, the software application on the second device controller 610B may be used to download the pattern file to the memory on-board the device 600. Subsequently, the interface may be used to replay the therapy pattern downloaded from the second device controller 610B. This may be done in a manner similar to the replay feature using touch sensing technology or conventional remote control interface on the second device controller 610B. In using this feature of interacting using a smart device, the user may prescribe a therapy pattern without the constraint of being in proximity or having to physically interact with the actual device. The pattern may be downloaded during the next availability of the device or perhaps even electronically transmitted to the user for him/her to download at his/her convenience. The second device controller 610B and the smart device 610C exemplify two different methods to interact with the device in an embodiment; however a practitioner in the art will recognize that these devices may be combined into one single input device or even split into multiple such devices depending on ease of use, manufacturability, or other such considerations. The essential feature is the combined functionality enabled by these input devices 610B and 610C in the embodiment disclosed herein.

According to another embodiment, the device can be pre-programmed based on the therapeutic requirements of the user. Several different spatio-temporal wave patterns may be created depending on therapeutic needs of the user. These default patterns may be pre-loaded to the controller memory at the time of manufacture of the device. A microcontroller can be used to achieve greater programmability. Alternately, dedicated circuitry may be used to provide a limited number of patterns thus providing the opportunity to manufacture the device at a reduced cost.

Each of the appended claims defines a specific portion of the invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims. No limitation with regard to the described aspects or embodiments of the present invention is intended. Many modifications to the depicted embodiments may be made without departing from the spirit and scope of the present invention. Accordingly, the foregoing description is intended to be illustrative rather than restrictive. The invention described herein is defined by the appended claims and all changes to the invention that fall within the meaning and the range of equivalency of the claims are embraced within their scope.

While the pain therapy device and methods of providing cold or heat-assisted distribution vibration therapy using the device are described in terms of "comprising," "containing," or "including" various components or steps, the wave vibration device and methods also can "consist essentially of" or "consist of" the various components and steps. Also, the terms in the claims have their plain, ordinary meaning unless otherwise explicitly and clearly defined by the patentee. Moreover, the indefinite articles "a", "an", and "the" as used herein and throughout the claims that follow are intended to include the plural references unless the context clearly indicates otherwise. Also, as used in the description herein, the meaning of "in" includes "in" and "on" unless the context clearly dictates otherwise. If there is any conflict in the usages of a word or term in this specification and one or more patent(s) or other documents that may be incorporated herein by reference, the definitions that are consistent with this specification should be adopted.

What is claimed is:

1. A device for masking pain at a target body part, the device comprising:
    a plurality of vibration motors, wherein each of the vibration motors is arranged along an actuatable grid located on a medium, wherein a spacing between a first vibration motor and a second vibration motor is a predetermined distance, wherein the medium is configured to be attached to the body part; and
    a vibration intensity parameter controller operatively coupled to the plurality of vibration motors, wherein the vibration intensity parameter controller is configured to designate a vibration amplitude and a frequency of each of the vibration motors; and
    a wave vibration therapy controller operatively coupled to the plurality of vibration motors wherein, at designated time intervals, the wave vibration therapy controller stimulates specific vibration motors arranged along the grid to generate a sensation of a wave vibration, and
    wherein the wave vibration therapy controller is configured to provide an automatic or built-in decay time to allow the target body part to react each time the wave vibration passes through, and
    wherein the wave vibration controller is configured to provide a radial wave that travels inward towards a trigger point where pain is concentrated and a radial ripple wave that travels outward from the trigger point.

2. The device according to claim 1, wherein the medium has a generally planar first surface, the first surface providing the plane of contact with the target body part.

3. The device according to claim 2, wherein the medium is made of a flexible material with an ability to conform to a body part of a user or another object in contact with a body part of the user.

4. The device according to claim 3, wherein the device further comprises a plurality of thermoelectric modules to provide active heating and cooling to the body part of the user, wherein the thermoelectric modules are attached to the medium using a thermally conductive adhesive layer.

5. The device according to claim 4, wherein one or more of the plurality of thermoelectric modules are positioned in series with one or more of the vibration motors for collocated pain therapy with heating and cooling.

6. The device according to claim 4, wherein one or more of the plurality of thermoelectric modules are positioned in parallel with the vibration motors for non-collocated vibration therapy with heating and cooling.

7. The device according to claim 2, wherein the vibrations are perpendicular to the first surface.

8. The device according to claim 7, wherein the device comprises a mechanism for regulating a predetermined temperature, frequency, amplitude, wave pattern, and time delay between waves.

9. The device according to claim 8, wherein the mechanism further enables pre-programming a specified pattern of the spatiotemporal wave for a playback, and further enables a user to review the pre-programmed wave pattern for confirmation prior to the playback via a user-interface.

10. The device according to claim 8, wherein the mechanism is a wired extension in operative communication with the controller, or is an extension in wireless communication with the device.

11. The device according to claim 8, wherein the mechanism comprises a touchpad screen or button interface to facilitate creation of the therapeutic wave pattern, and regulate a predetermined temperature, frequency, amplitude, wave pattern, and time delay between waves.

12. The device according to claim 1, wherein the vibration motors are electro-mechanically driven and heat of the electro-mechanically driven vibration motors provides passive heating of the body part of the user.

13. The device according to claim 12, wherein the electro-mechanically driven vibration motors are selected from a group consisting of a coin shaped motor and a disc shaped motor.

14. A method for masking pain, the method comprising steps of:
    providing a device having a medium for attachment to a target body part;
    arranging a plurality of vibration motors along a grid pattern on the medium;
    facilitating movement of the vibration motors along a Z axis, wherein a plane of attachment of the medium and the body part of the user are along a X-Y axis;
    designating a vibration amplitude and a frequency for each of the vibration motors;
    creating a sensation of a wave vibration by stimulating specific vibration motors arranged along the grid at designated time intervals, wherein the sensation of the wave vibration modulates a perception of pain;
    facilitating an automatic or built-in decay time to allow for a tissue to react each time the wave passes through; and
    wherein the wave vibration created comprises a radial wave that travels inward towards a trigger point where pain is concentrated and a radial ripple wave that travels outward from the trigger point.

15. The method according to claim 14, wherein the vibrations are perpendicular to a surface in contact with a target body part.

16. The method according to claim 15, further comprising altering the amplitude, the frequency and a speed of the wave vibrations.

17. The method according to claim 16, further comprising pre-programming a wave pattern, a trigger point, the amplitude, the frequency and the speed of the wave vibrations, and the automatic decay time between the wave vibrations for a playback.

18. The method according to claim 17, further comprising reviewing the pre-programmed wave pattern for confirmation prior to the playback.

19. The method according to claim 14, further comprising creating waves that travel substantially sideways.

20. The method according to claim 14, further comprising creating waves that travel horizontally.

21. The method according to claim 14, further comprising creating waves that travel substantially vertically.

22. The method according to claim 14, further comprising creating a combination therapy pattern, wherein the combination therapy pattern has waves that travel radially, in a ripple pattern, substantially sideways, horizontally and substantially vertically.

\* \* \* \* \*